(12) United States Patent
Miyoshi

(10) Patent No.: US 10,258,223 B2
(45) Date of Patent: Apr. 16, 2019

(54) INSERTING INSTRUMENT, ROTARY UNIT AND INSERTING APPARATUS

(71) Applicant: OLYMPUS CORPORATION, Tokyo (JP)

(72) Inventor: Hiroaki Miyoshi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/153,906

(22) Filed: May 13, 2016

(65) Prior Publication Data

US 2016/0249787 A1 Sep. 1, 2016

Related U.S. Application Data

(63) Continuation of application No. PCT/JP2014/075685, filed on Sep. 26, 2014.

(30) Foreign Application Priority Data

Nov. 14, 2013 (JP) .................................. 2013-236317

(51) Int. Cl.
*A61B 1/005* (2006.01)
*A61B 1/01* (2006.01)
(Continued)

(52) U.S. Cl.
CPC .......... *A61B 1/0055* (2013.01); *A61B 1/0016* (2013.01); *A61B 1/00073* (2013.01); *A61B 1/00133* (2013.01); *A61B 1/05* (2013.01)

(58) Field of Classification Search
CPC .............. A61B 1/00156; A61B 1/0016; A61B 1/00154; A61B 1/0055; A61B 1/05; A61B 1/0013; A61B 1/00073
See application file for complete search history.

(56) References Cited

U.S. PATENT DOCUMENTS

2006/0111617 A1\* 5/2006 Wimmer .............. A61B 1/0055 600/146
2013/0035552 A1\* 2/2013 Moriyama ......... A61B 1/00073 600/149

(Continued)

FOREIGN PATENT DOCUMENTS

JP 2004-141665 A 5/2004
JP 2004-209267 A 7/2004

(Continued)

OTHER PUBLICATIONS

International Preliminary Report on Patentability together with the Written Opinion from related International Application No. PCT/JP2014/075685 dated May 26, 2016.

(Continued)

*Primary Examiner* — John P Leubecker
*Assistant Examiner* — Genja Frankert
(74) *Attorney, Agent, or Firm* — Scully, Scott, Murphy & Presser, P.C.

(57) ABSTRACT

An inserting instrument includes a first flexible tube section having a flexibility lower than a spiral tube, a second flexible tube section having a flexibility lower than the spiral tube and equal to or higher than the first flexible tube section in a state where the second flexible tube section is not covered with the spiral tube. The flexibility of the second flexible tube section is lower than that of the first flexible tube section when the second flexible tube section is covered with the spiral tube. The inserting instrument includes a third flexible tube section provided on the proximal direction side with respect to the second flexible tube section and having a flexibility lower than the first flexible tube section.

9 Claims, 9 Drawing Sheets

(51) Int. Cl.
*A61B 1/00* (2006.01)
*A61B 1/05* (2006.01)

(56) References Cited

U.S. PATENT DOCUMENTS

2013/0041222 A1    2/2013  Moriyama
2013/0109919 A1*   5/2013  Sugiyama .......... A61B 1/00071
                                              600/117

FOREIGN PATENT DOCUMENTS

| JP | 2009-226023 A | 10/2009 | | |
|----|---------------|---------|---|---|
| JP | 2010-167101 A | 8/2010 | | |
| JP | 2011-520563 A | 7/2011 | | |
| JP | WO 2012137362 A1 * | 10/2012 | ......... | A61B 1/00073 |
| JP | 2013-027466 A | 2/2013 | | |
| WO | WO 2012/137361 A1 | 10/2012 | | |
| WO | WO 2012/137362 A1 | 10/2012 | | |
| WO | WO 2012/137363 A1 | 10/2012 | | |
| WO | WO 2012/137365 A1 | 10/2012 | | |

OTHER PUBLICATIONS

International Search Report dated Jan. 6, 2015 issued in PCT/JP2014/075685.
Japanese Office Action dated Aug. 25, 2015 issued in JP 2015-533352.
Extended Supplementary European Search Report dated Aug. 8, 2017 received in European Patent Application No. 14 86 1452.2.
European Search Report dated Feb. 22, 2019 received in European Patent Application No. 14 861 452.2.

* cited by examiner

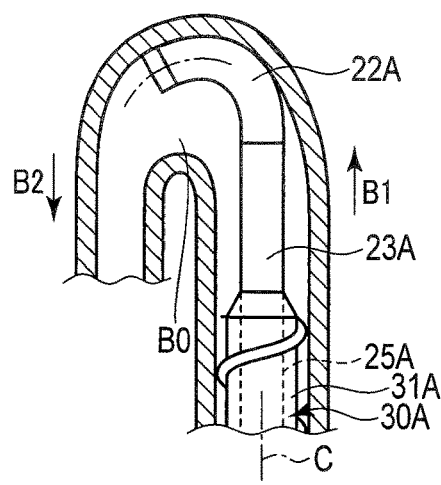
F I G. 8
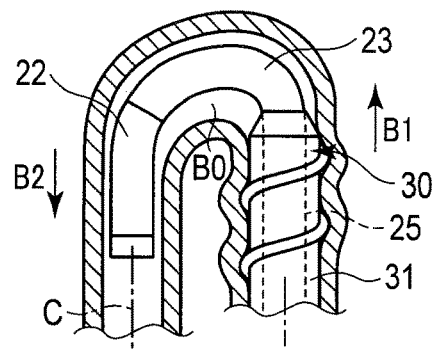
F I G. 9
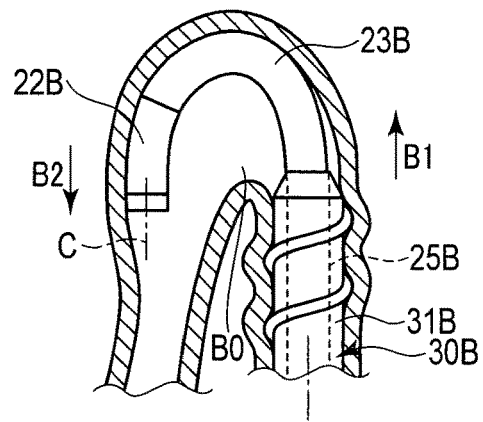
F I G. 10

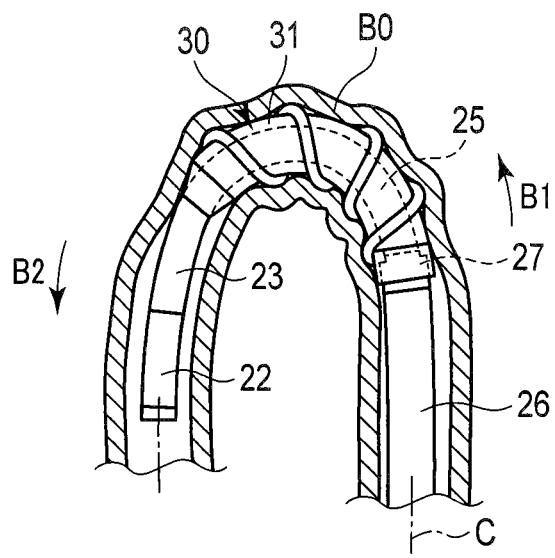
F I G. 11
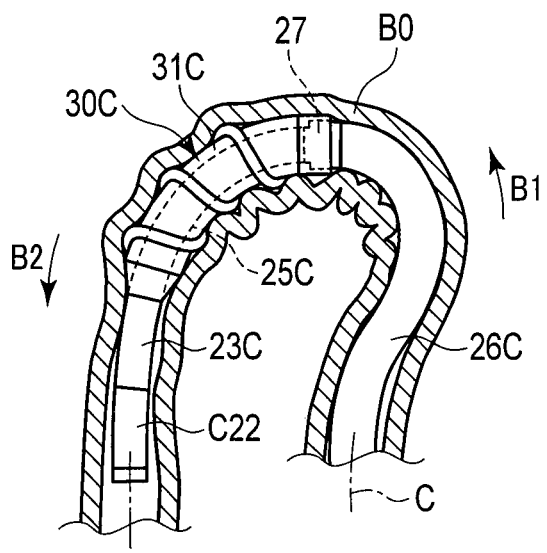
F I G. 12

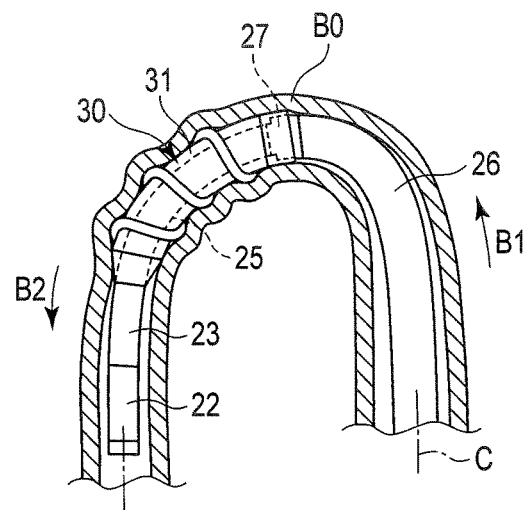
F I G. 13
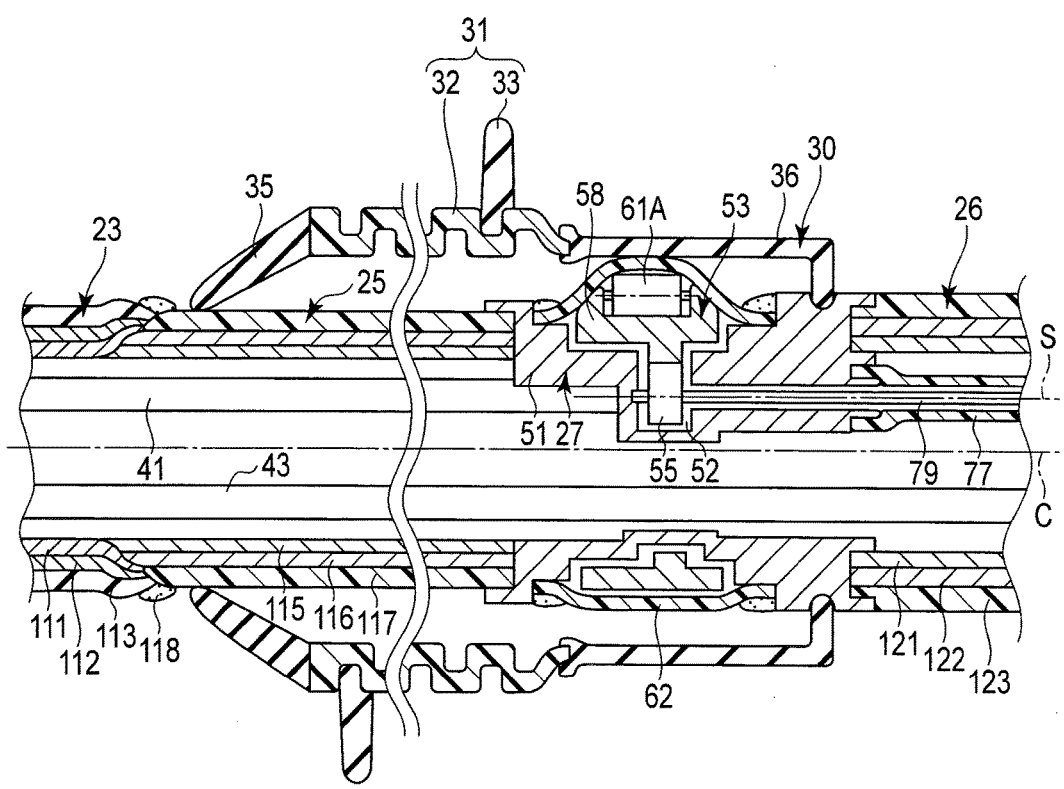
F I G. 14

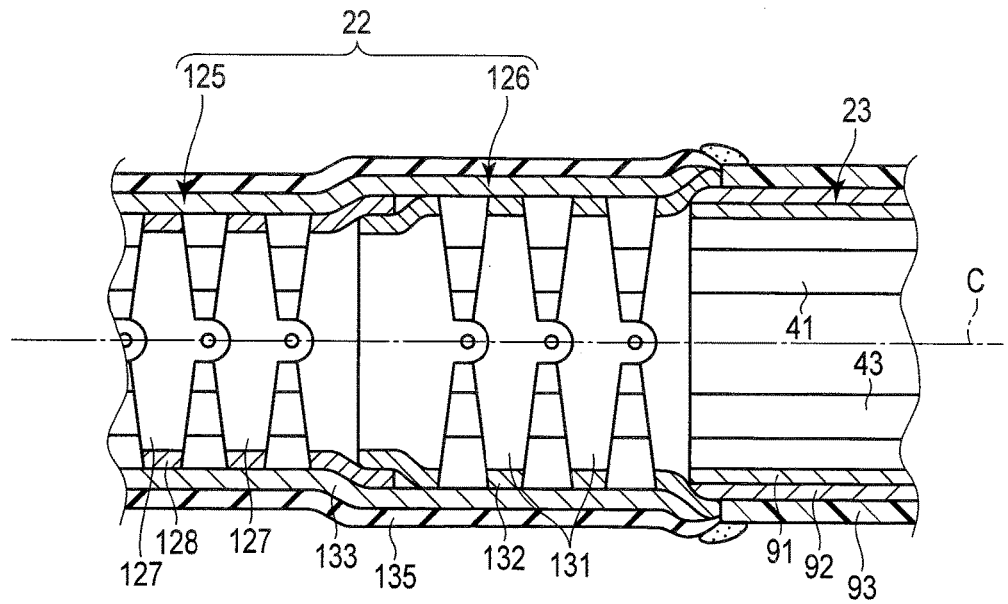
F I G. 15
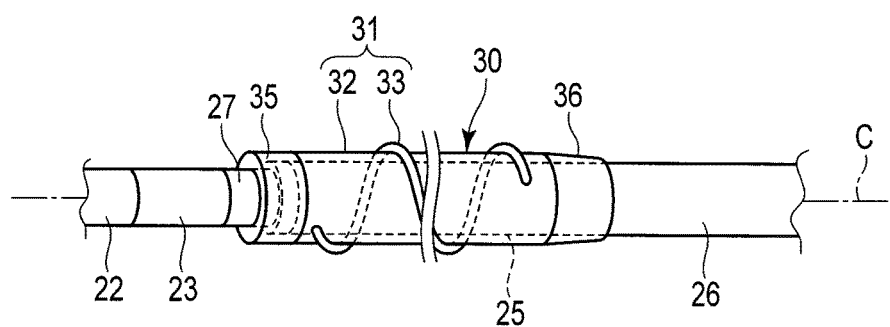
F I G. 16

INSERTING INSTRUMENT, ROTARY UNIT AND INSERTING APPARATUS

CROSS-REFERENCE TO RELATED APPLICATIONS

This is a Continuation Application of PCT Application No. PCT/JP2014/075685, filed Sep. 26, 2014 and based upon and claiming the benefit of priority from prior Japanese Patent Application No. 2013-236317, filed Nov. 14, 2013, the entire contents of which are incorporated herein by reference.

BACKGROUND OF THE INVENTION

1. Field of the Invention

The present invention relates to an inserting instrument to which a rotary unit including a spiral tube is rotatably attached around a longitudinal axis. Further, it relates to a rotary unit to be attached to the inserting instrument, and an inserting apparatus including the inserting instrument and the rotary unit.

2. Description of the Related Art

In Jpn. Pat. Appln. KOKAI Publication No. 2011-520563, there is disclosed an endoscope that is an inserting instrument including an inserting section to which a rotary unit including a spiral tube is rotatably attached around a longitudinal axis. In this endoscope, the inserting section is inserted through the rotary unit. The inserting section includes an intermediate region covered with the rotary unit from an outer peripheral side, a far region (a distal region) disposed on a distal direction side with respect to the intermediate region, and a near region (a proximal region) disposed on a proximal direction side with respect to the intermediate region. The far region and the near region are not covered with the rotary unit. In the endoscope, the rotary unit rotates in a state where the spiral tube is pressed from a lumen wall toward an inner peripheral direction, whereby an impulsive force in a distal direction or an impulsive force in a proximal direction acts on the inserting section and the rotary unit.

BRIEF SUMMARY OF THE INVENTION

According to one aspect of the invention, an inserting instrument to which a rotary unit including a spiral tube is rotatably attached around a longitudinal axis, the inserting instrument including: an inserting section extended along the longitudinal axis, and inserted through the rotary unit; a bending section provided in a distal portion of the inserting section; a first flexible tube section provided on a proximal side with respect to the bending section in the inserting section, and having a flexibility lower than each the spiral tube and the bending section; a second flexible tube section provided on the proximal side with respect to the first flexible tube section in the inserting section, and covered by the spiral tube on an outer peripheral side in a state where the rotary unit is attached to the inserting section, the second flexible tube section having a flexibility lower than a flexibility of the spiral tube and the flexibility equal to that of the first flexible tube section or higher than that of the first flexible tube section in a state where the second flexible tube section is not covered by the spiral tube, the flexibility of the second flexible tube section being formed to be lower than the first flexible tube section in a state where the second flexible tube section is covered by the spiral tube; and a third flexible tube section provided on the proximal side with respect to the second flexible tube section in the inserting section, having a flexibility lower than the first flexible tube section, and formed in a state where the flexibility decreases from a distal side toward the proximal side, wherein a flexibility at a proximal end of the third flexible tube section is adjusted to be lowest in the first flexible tube section, the second flexible tube section and the third flexible tube section, and the flexibility of the second flexible tube section in the state where the second flexible tube section is covered by the spiral tube is adjusted to be higher than the flexibility at the proximal end of the third flexible tube section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a schematic view showing a state where an impulsive force toward a distal direction is applied to an inserting section from a state where a distal end of a first flexible tube section is positioned in a lumen bending site according to a first comparative example;

FIG. 9 is a schematic view showing a state where an impulsive force toward a distal direction is applied to an inserting section from a state where a distal end of the first flexible tube section is positioned in a lumen bending site according to the first embodiment;

FIG. 10 is a schematic view showing a state where an impulsive force toward a distal direction is applied to an inserting section from a state where a distal end of a second flexible tube section covered with a spiral tube is positioned in a lumen bending site according to a second comparative example;

FIG. 11 is a schematic view showing the state where the impulsive force toward the distal direction is applied to the inserting section from a state where a distal end of the second flexible tube section covered with the spiral tube is positioned in the lumen bending site according to the first embodiment;

FIG. 12 is a schematic view showing a state where an impulsive force toward a distal direction is applied to an inserting section from a state where a distal portion of a third flexible tube section is positioned in a lumen bending site according to a third comparative example;

FIG. 13 is a schematic view showing a state where the impulsive force toward the distal direction is applied to the inserting section from a state where a distal portion of the third flexible tube section is positioned in the lumen bending site according to the first embodiment;

FIG. 14 is a cross-sectional view schematically showing a constitution of a first flexible tube section, a second flexible tube section, a third flexible tube section and a rotary unit according to a first modification;

FIG. 15 is a cross-sectional view schematically showing a constitution of a bending section and a first flexible tube section according to a second modification; and FIG. 16 is a perspective view schematically showing a constitution of an inserting section and a rotary unit according to a third modification.

DETAILED DESCRIPTION OF THE INVENTION

First Embodiment

Figure 1:
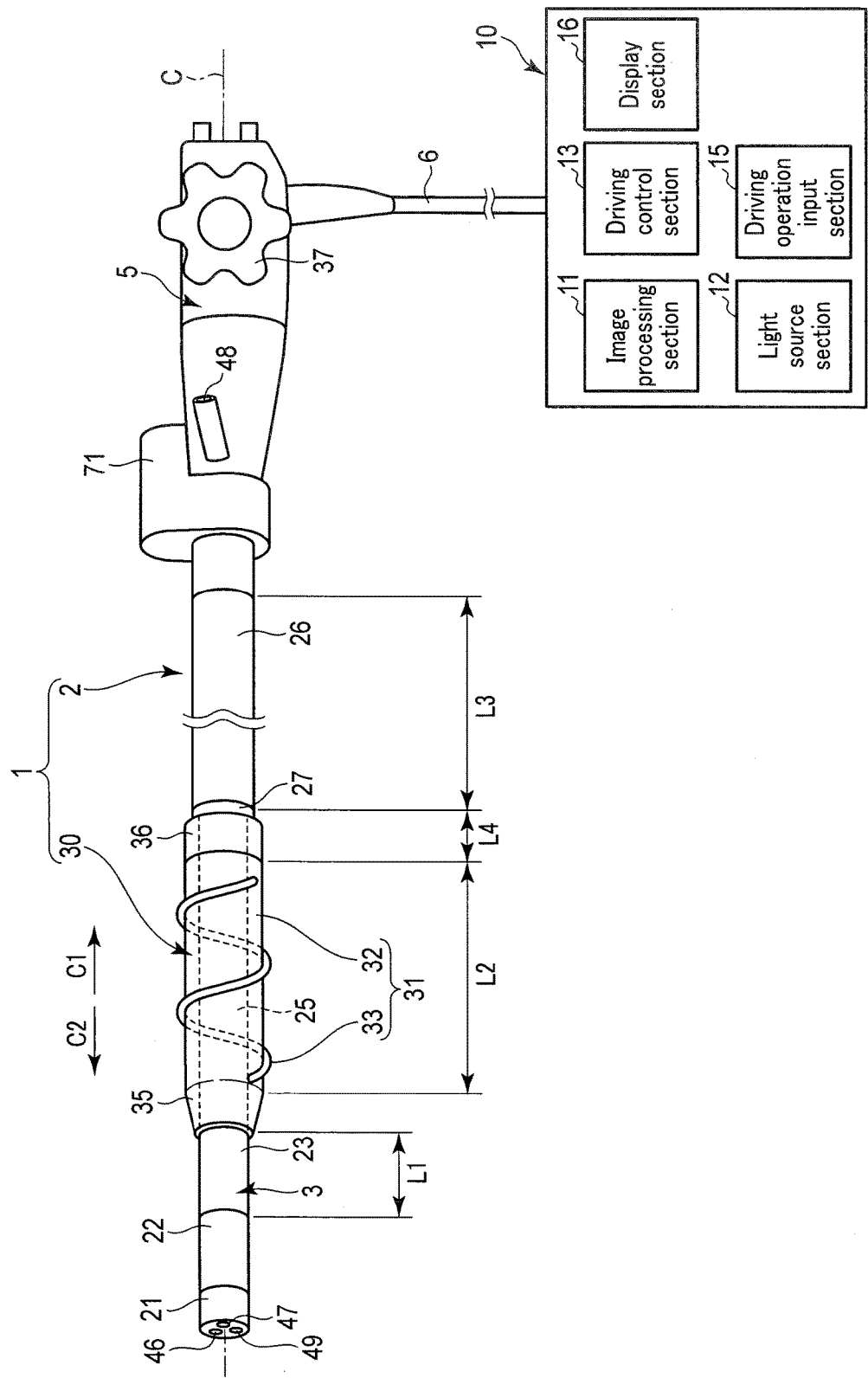
FIG. 1 is a schematic view showing an endoscope apparatus according to a first embodiment of the present invention.

A first embodiment of the present invention will be described with reference to FIG. 1 to FIG. 14. FIG. 1 is a view showing an endoscope apparatus 1 that is an inserting apparatus according to the first embodiment. As shown in FIG. 1, the endoscope apparatus 1 has a longitudinal axis C. One of directions parallel to the longitudinal axis C (a direction of an arrow C1 of FIG. 1) is a proximal direction, and an opposite direction to the proximal direction (a direction of an arrow C2 of FIG. 1) is a distal direction. Further, the distal direction and the proximal direction are axis parallel directions parallel to the longitudinal axis C. The endoscope device 1 includes an endoscope 2 that is an inserting instrument. The endoscope 2 includes an inserting section (an endoscope inserting section) 3 extended along the longitudinal axis C, and an operating section (an endoscope operating section) 5 disposed on the proximal direction side with respect to the inserting section 3. The inserting section 3 is extended along the longitudinal axis C, and inserted into a body cavity when the endoscope apparatus 1 is used.

The operating section 5 is connected to one end of a universal cord 6. The other end of the universal cord 6 is connected to a peripheral unit 10. The peripheral unit 10 includes an image processing section 11 such as an image processor, a light source section 12 including a light source such as a lamp, a driving control section 13 that is a control device including, for example, an electric power source, a storage section such as a memory and a CPU (central processing unit) or an ASIC (application specific integrated circuit), a driving operation input section 15 such as a button or a foot switch, and a display section 16 such as a monitor.

The inserting section 3 includes a distal rigid section 21 that forms a distal end of the inserting section 3, a bending section 22 disposed on the proximal direction side with respect to the distal rigid section 21, a first flexible tube section 23 provided on the proximal direction side from the bending section 22, a second flexible tube section 25 disposed on the proximal direction side with respect to the first flexible tube section 23, and a third flexible tube section 26 disposed on the proximal direction side with respect to the second flexible tube section 25. As to the axis parallel direction parallel to the longitudinal axis C, a base section 27 is provided between the second flexible tube section 25 and the third flexible tube section 26. The second flexible tube section 25 is coupled with the third flexible tube section 26 via the base section 27.

A first axis parallel dimension L1 of the first flexible tube section 23 in the axis parallel direction parallel to the longitudinal axis C is smaller than a second axis parallel dimension L2 of the second flexible tube section 25 in the axis parallel direction. Additionally, the second axis parallel dimension L2 of the second flexible tube section 25 in the axis parallel direction is smaller than a third axis parallel dimension L3 of the third flexible tube section 26 in the axis parallel direction. Furthermore, a fourth axis parallel dimension L4 of the base section 27 in the axis parallel direction is smaller than the first axis parallel dimension L1.

Here, in a cross section perpendicular to the longitudinal axis C, a direction away from the longitudinal axis C is defined as an outer peripheral direction (a direction away from the axis) and a direction toward the longitudinal axis C is defined as an inner peripheral direction (a direction toward the axis). On an outer peripheral side of the inserting section 3, a cylindrical rotary unit 30 is disposed. The rotary unit 30 is attached to the inserting section 3 of the endoscope 2 in a state where the inserting section 3 is inserted through the rotary unit 30. In the state where the rotary unit 30 is attached to the inserting section 3, the rotary unit 30, to which a rotation driving force is transmitted, rotates relative to the inserting section 3 about the longitudinal axis C.

The rotary unit 30 includes a spiral tube 31 extended along the longitudinal axis C. The spiral tube 31 includes a corrugate tube portion 32 and a fin portion 33 extended on an outer peripheral surface of the corrugate tube portion 32. The fin portion 33 is helically extended around the longitudinal axis C from the proximal direction toward the distal direction. A distal side cylindrical portion 35 is provided on a distal direction side of the spiral tube 31. The distal side cylindrical portion 35 is formed into a tapered shape whose outer diameter decreases toward the distal direction side. Additionally, a cylindrical proximal side cylindrical portion 36 is disposed on a proximal direction side of the spiral tube 31.

In a state where the fin portion 33 of the spiral tube 31 is pressed in the inner peripheral direction by a lumen wall or the like, the rotary unit 30 rotates around the longitudinal axis C, thereby applying an impulsive force in the distal direction or the proximal direction to the inserting section 3 and the rotary unit 30. By the impulsive force toward the distal direction, there improves a movability of the inserting section 3 toward an inserting direction (the distal direction) in a lumen such as an inner part of a small intestine or an inner part of a large intestine, and by the impulsive force toward the proximal direction, there improves a movability of the inserting section 3 toward a pullout direction (the proximal direction) in the lumen.

Figure 2:
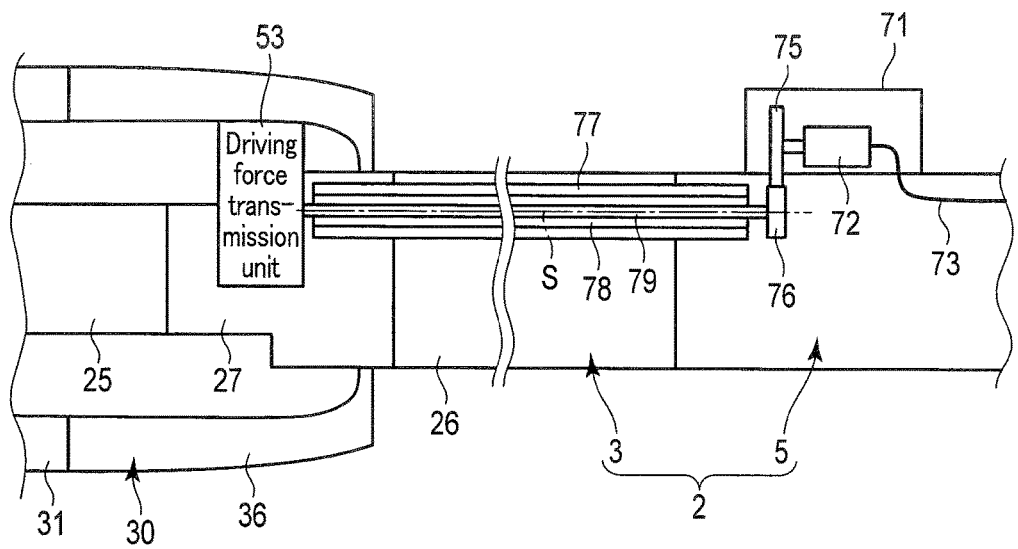
FIG. 2 is a schematic view showing a constitution to transmit a rotation driving force to a rotary unit according to the first embodiment.
Figure 3:
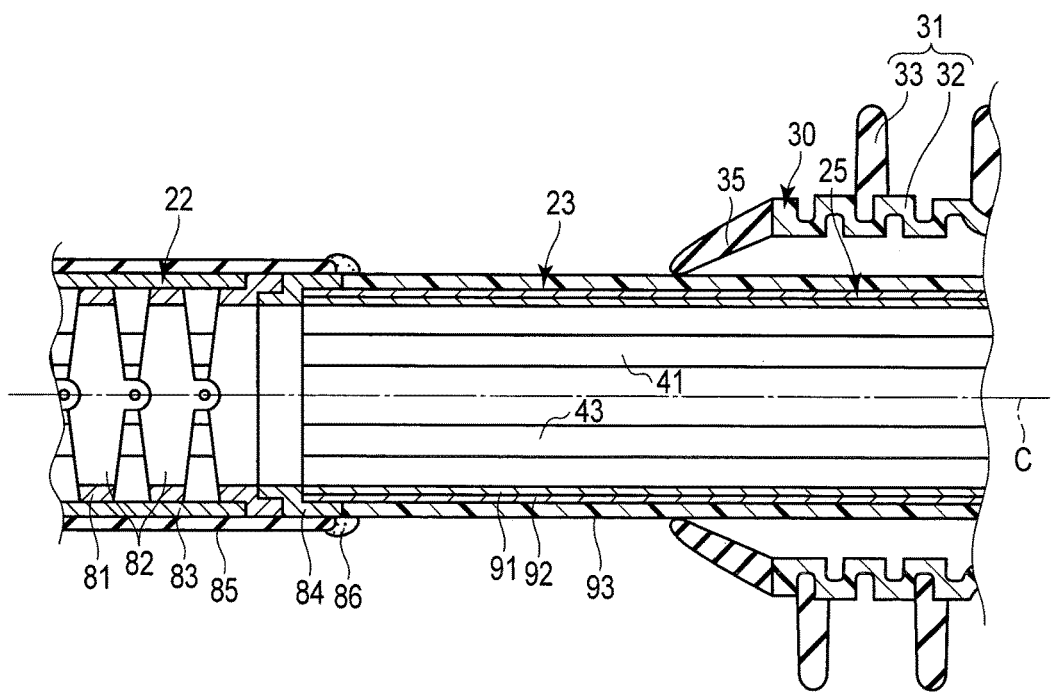
FIG. 3 is a cross-sectional view schematically showing a constitution of a bending section, a first flexible tube section, a second flexible tube section and the rotary unit according to the first embodiment.
Figure 4:
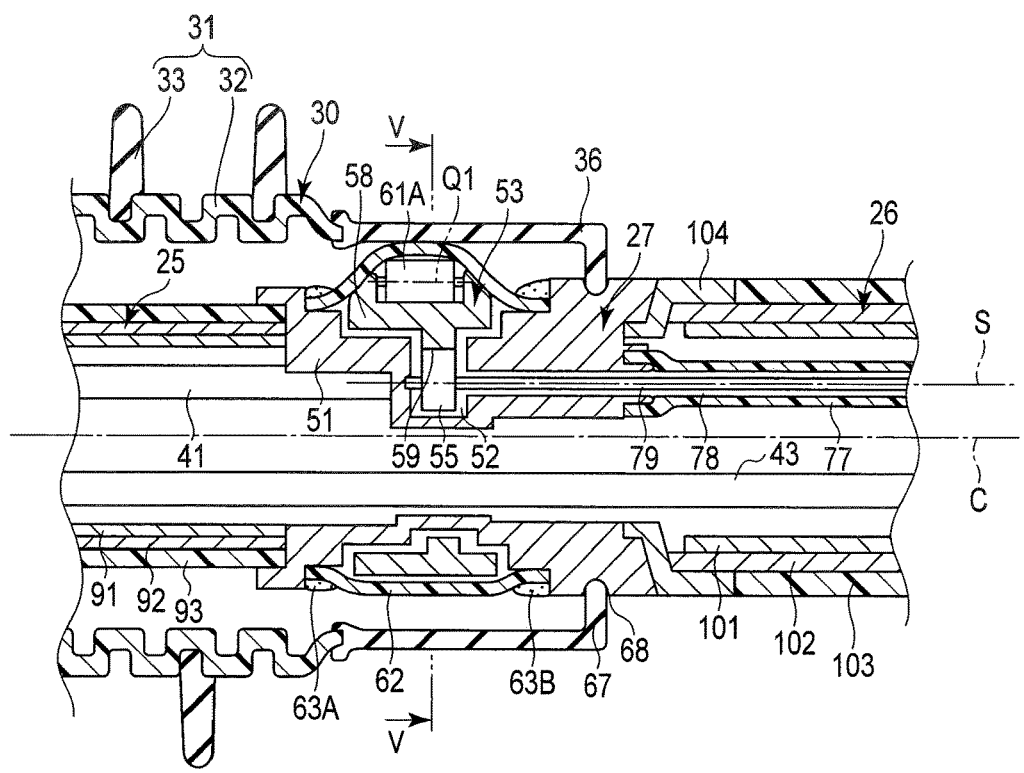
FIG. 4 is a cross-sectional view schematically showing a constitution of the second flexible tube section, a third flexible tube section, a base section and the rotary unit according to the first embodiment.

FIG. 2 is a view showing a constitution to transmit the rotation driving force to the rotary unit 30. FIG. 3 is a view showing a constitution of the bending section 22, the first flexible tube section 23, the second flexible tube section 25 and the rotary unit 30. FIG. 4 is a view showing a constitution of the second flexible tube section 25, the third flexible tube section 26, the base section 27 and the rotary unit 30. Additionally, FIG. 5 is a cross-sectional view of FIG. 4 taken along the V-V line.

As shown in FIG. 1, on an outer surface of the operating section 5, a bending operation knob 37 is disposed in which a bending operation of the bending section 22 is input. As shown in FIG. 5, inside the inserting section 3, bending wires 38A and 38B are extended along the longitudinal axis C. Inside the operating section 5, proximal ends of the bending wires 38A and 38B are connected to a pulley (not shown) coupled with the bending operation knob 37. Distal ends of the bending wires 38A and 38B are connected to a distal portion of the bending section 22. By the bending operation with the bending operation knob 37, the bending wire 38A or the bending wire 38B is pulled and the bending section 22 bends. In the present embodiment, the bending section 22 is constituted only of an active bending section that bends by the bending operation.

Each of the bending wires 38A and 38B is inserted into a corresponding coil 39A or 39B. Proximal ends of the coils 39A and 39B are extended into the operating section 5. Additionally, distal ends of the coils 39A and 39B are connected to an inner peripheral surface of a distal portion of the first flexible tube section 23. It is to be noted that in the present embodiment, two bending wires 38A and 38B are disposed and the bending section 22 is bendable in two directions, but, for example, four bending wires may be provided and the bending section 22 may be bendable in four directions.

Figure 5:
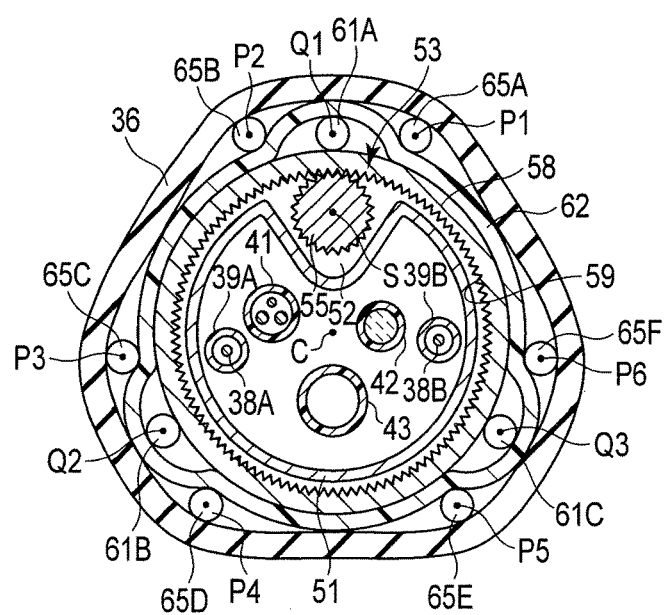
FIG. 5 is a cross-sectional view of FIG. 4 taken along the V-V line.

As shown in FIG. 3 to FIG. 5, an imaging cable 41, a light guide 42 and a channel tube 43 are extended along the longitudinal axis C inside the inserting section 3. Inside the distal rigid section 21 (a distal portion of the inserting section 3), an imaging element (not shown) configured to image a subject is disposed. The imaging element images the subject through an observation window 46. One end of the imaging cable 41 is connected to the imaging element. The imaging cable 41 is extended through the inside of the inserting section 3, the inside of the operating section 5 and an inside of the universal cord 6 and the other end of the imaging cable is connected to the image processing section 11 of the peripheral unit 10. The image processing section 11 performs image processing of the imaged subject image and the image of the subject is generated. Further, the generated image of the subject is displayed in the display section 16.

Additionally, the light guide 42 is extended through the inside of the inserting section 3, the inside of the operating section 5 and the inside of the universal cord 6 and connected to the light source section 12 of the peripheral unit 10. Light emitted from the light source section 12 is guided by the light guide 42 and the subject is irradiated from an illumination window 47 of the distal portion of the inserting section 3 (the distal rigid section 21).

As shown in FIG. 1, on the outer surface of the operating section 5, a treatment tool inserting portion 48 is disposed into which a treatment tool such as forceps is inserted. The channel tube 43 extends through the inside of the inserting section 3 and the inside of the operating section 5 and one end of the channel tube is connected to the treatment tool inserting portion 48. The treatment tool inserted from the treatment tool inserting portion 48 extends through an inside of the channel tube 43 and projects from an opening 49 of the distal rigid section 21 toward the distal direction. Further, in a state where the treatment instrument is projected from the opening 49 of the distal rigid section 21, a treatment by use of the treatment tool is performed.

As shown in FIG. 4, in the base section 27, a support member 51 made of a metal is provided. A proximal portion of the second flexible tube section 25 is coupled with a distal portion of the support member 51. Additionally, a distal portion of the third flexible tube section 26 is coupled with a proximal portion of the support member 51. Consequently, the second flexible tube section 25 is connected to the third flexible tube section 26 via the base section 27.

As shown in FIG. 4 and FIG. 5, in the base section 27, a hollow portion 52 is defined by the support member 51. Additionally, a driving force transmission unit 53 is attached to the support member 51. The driving force transmission unit 53 is disposed in the hollow portion 52. Additionally, the driving force transmission unit 53 is driven by the transmission of the rotation driving force to drive the rotary unit 30. The driving force transmission unit 53 includes a driving gear 55.

Additionally, the driving force transmission unit 53 includes a rotary cylindrical member 58. The rotary cylindrical member 58 is attached to the base section 27 in a state where the support member 51 is inserted through the rotary cylindrical member 58. The rotary cylindrical member 58 is rotatable relative to the inserting section 3 (the base section 27) about the longitudinal axis C. Here, two directions in which the rotary unit 30 rotates are defined as periaxial directions of the longitudinal axis. On an inner peripheral surface of the rotary cylindrical member 58, an inner peripheral gear portion 59 is disposed along the whole periphery in the periaxial direction of the longitudinal axis. The inner peripheral gear portion 59 meshes with the driving gear 55.

In the present embodiment, three inner rollers 61A to 61C are attached to the rotary cylindrical member 58. The inner rollers 61A to 61C are disposed away from one another by a substantially equal space in the periaxial direction of the longitudinal axis. The inner rollers 61A to 61C have corresponding roller axes (Q1 to Q3), respectively. The respective inner rollers 61A to 61C are rotatable relative to the rotary cylindrical member 58 about the corresponding roller axes (Q1 to Q3). Additionally, the inner rollers 61A to 61C are rotatable relative to the inserting section 3 (the base section 27) integrally with the rotary cylindrical member 58 around the longitudinal axis C.

The rotary cylindrical member 58 and the inner rollers 61A to 61C are covered with a cylindrical cover member 62 from their outer peripheral sides. A distal end of the cover member 62 is fixed to an outer peripheral surface of the support member 51 via a bonding portion 63A such as an adhesive and a proximal end of the cover member 62 is fixed to the outer peripheral surface of the support member 51 via a bonding portion 63B such as the adhesive. By the cover member 62, the hollow portion 52 in which the driving force transmission unit 53 is disposed is separated from the outside of the inserting section 3. At a fixed position of the distal end of the cover member 62 and a fixed position of the proximal end of the cover member 62, a space between the support member 51 and the cover member 62 is liquid-tightly kept. Consequently, inflow of a liquid from the outside of the inserting section 3 into the hollow portion 52 and the driving force transmission unit 53 is prevented. Additionally, in regions in which the inner rollers 61A to 61C are positioned in the periaxial direction of the longitudinal axis, the cover member 62 projects toward the outer peripheral direction. It is to be noted that the cover member 62 is fixed to the inserting section 3, and the rotary cylindrical member 58 and the inner rollers 61A to 61C are rotatable relative to the cover member 62 in the periaxial direction of the longitudinal axis.

As shown in FIG. 5, six outer rollers 65A to 65F are attached to an inner peripheral surface of the proximal side cylindrical portion 36. The outer rollers 65A to 65F are positioned on an outer peripheral side of the cover member 62. In the state where the rotary unit 30 is attached to the inserting section 3, the inner roller 61A is positioned between the outer roller 65A and the outer roller 65B in the periaxial direction of the longitudinal axis and the inner roller 61B is positioned between the outer roller 65C and the outer roller 65D in the direction around the longitudinal axis. Additionally, the inner roller 61C is positioned between the outer roller 65E and the outer roller 65F in the periaxial direction of the longitudinal axis. The outer rollers 65A to 65F have corresponding roller axes (P1 to P6), respectively. The respective outer rollers 65A to 65F are rotatable relative to the cover member 62 and the proximal side cylindrical portion 36 about the corresponding roller axes (P1 to P6). Additionally, the outer rollers 65A to 65F are rotatable to the inserting section 3 (the base section 27) integrally with the rotary unit 30 around the longitudinal axis C.

The driving force transmission unit 53 is driven by the rotation driving force, whereby the rotary cylindrical member 58 rotates about the longitudinal axis C. Consequently, the inner roller 61A presses the outer roller 65A or the outer roller 65B. Similarly, the inner roller 61B presses the outer roller 65C or the outer roller 65D and the inner roller 61C presses the outer roller 65E or the outer roller 65F. In consequence, the driving force is transmitted from the inner rollers 61A to 61C to the outer rollers 65A to 65F of the rotary unit 30 and the rotary unit 30 rotates relative to the inserting section 3 and the cover member 62 around the longitudinal axis C. As described above, the outer rollers 65A to 65F attached to the proximal side cylindrical portion 36 become driving force receiving portions configured to receive the rotation driving force from the driven driving force transmission unit 53. The outer rollers 65A to 65F that are the driving force receiving portions are disposed on the proximal direction side with respect to the spiral tube 31. Additionally, in the state where the rotary unit 30 is attached to the inserting section 3, the outer rollers 65A to 65F are positioned on an outer peripheral side of the base section 27.

It is to be noted that the respective inner rollers 61A to 61C rotate about the corresponding roller axes (Q1 to Q3), and hence friction between each of the inner rollers 61A to 61C and the cover member 62 decreases. Similarly, the respective outer rollers 65A to 65F rotate about the corresponding roller axes (P1 to P6), and hence friction between each of the outer rollers 65A to 65F and the cover member 62 decreases. In consequence, the rotation driving force is appropriately transmitted from the inner rollers 61A to 61C to the rotary unit 30 and the rotary unit 30 appropriately rotates.

In the proximal side cylindrical portion 36, an engaging pawl 67 that projects in the inner peripheral direction is provided. Additionally, in the support member 51 of the base section 27, an engaging groove 68 is provided along the whole periphery in the periaxial direction of the longitudinal axis. The engaging pawl 67 engages with the engaging groove 68, whereby movement of the rotary unit 30 relative to the inserting section 3 along the longitudinal axis C is regulated. Additionally, in a state where the engaging pawl 67 is engaged with the engaging groove 68, the engaging pawl 67 is movable relative to the engaging groove 68 in the periaxial direction of the longitudinal direction.

As shown in FIG. 1 and FIG. 2, the operating section 5 is coupled with a motor housing 71. Inside the motor housing 71, a motor 72 that is a driving source is housed. The motor 72 is connected to one end of a motor cable 73. The motor cable 73 is extended through the inside of the operating section 5 and the inside of the universal cord 6 and the other end of the motor cable is connected to the driving control section 13 of the peripheral unit 10. An electric power is supplied from the driving control section 13 via the motor cable 73, thereby driving the motor 72. By driving the motor 72, the rotation driving force to rotate the rotary unit 30 is generated. A relay gear 75 is attached to the motor 72. Additionally, inside the operating section 5, a driving gear 76 that meshes with the relay gear 75 is disposed.

As shown in FIG. 2 and FIG. 4, a guide tube 77 is extended along the longitudinal axis C inside the third flexible tube section 26 of the inserting section 3. A distal end of the guide tube 77 is connected to the support member 51 of the base section 27. Inside the guide tube 77, a guide channel 78 is formed. A distal end of the guide channel 78 communicates with the hollow portion 52. In the guide channel 78, a driving shaft 79 that is a line portion is extended along a shaft axis S. The rotation driving force generated in the motor 72 is transmitted to the driving shaft 79 via the relay gear 75 and the driving gear 76. The rotation driving force is transmitted to the driving shaft 79, whereby the driving shaft 79 rotates about the shaft axis S.

A distal end of the driving shaft 79 is connected to the driving gear 55 of the driving force transmission unit 53. The driving shaft 79 rotates, thereby transmitting the rotation driving force to the driving force transmission unit 53, and the driving force transmission unit 53 is driven. Further, the rotation driving force is transmitted to the rotary cylindrical member 58, whereby the rotation driving force is transmitted to the rotary unit 30 as described above. In consequence, the rotary unit 30 rotates.

As shown in FIG. 3, the bending section 22 includes a bending tube 81. The bending tube 81 includes bending pieces 82 made of a metal. Each of the bending pieces 82 is rotatably coupled with the adjacent bending piece 82. In the bending section 22, an outer peripheral side of the bending tube 81 is covered with a bending reticular tube 83 that is a bending blade. In the bending reticular tube 83, a wire (not shown) made of a metal is reticularly knitted. Additionally, in the bending section 22, an outer peripheral side of the bending reticular tube 83 is covered with a bending envelope 85. The bending envelope 85 is made of, for example, a fluororubber.

Figure 6:
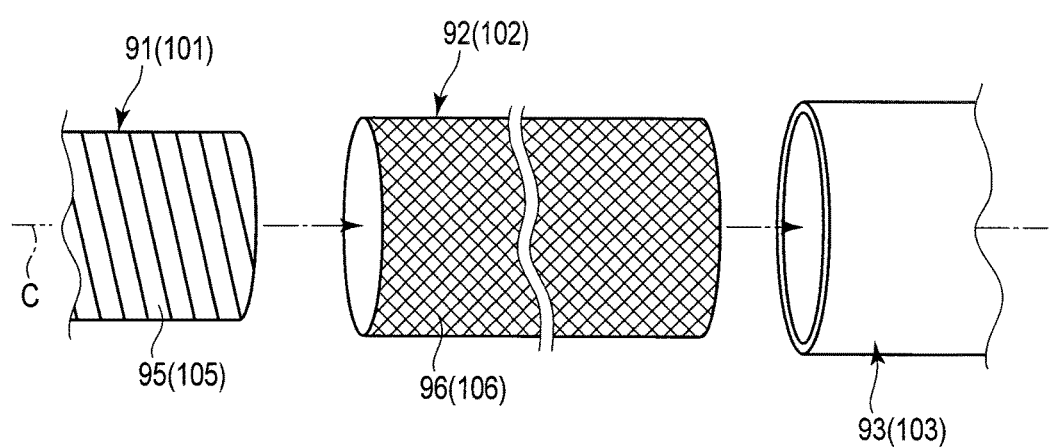
FIG. 6 is an exploded perspective view schematically showing members of the first flexible tube section and the second flexible tube section (the third flexible tube section) according to the first embodiment.

FIG. 6 is an exploded view of members of the first flexible tube section 23 and the second flexible tube section 25. As shown in FIG. 3, FIG. 4 and FIG. 6, in the present embodiment, the first flexible tube section 23 and the second flexible tube section 25 are constituted of a first helical tube 91 that is a first flex, a first flexible reticular tube 92 that is a first flexible blade, and a first flexible envelope 93. The first helical tube 91, the first flexible reticular tube 92 and the first flexible envelope 93 are extended along the longitudinal axis C from a distal end of the first flexible tube section 23 to a proximal end of the second flexible tube section 25. An outer peripheral side of the first helical tube 91 is covered with the first flexible reticular tube 92, and an outer peripheral side of the first flexible reticular tube 92 is covered with the first flexible envelope 93.

A proximal portion of the bending tube 81 is fitted into a cylindrical connecting tube 84. The first helical tube 91 and the first flexible reticular tube 92, which are inserted into an inner peripheral side of the connecting tube 84, are fitted into the connecting tube 84. Additionally, the first flexible envelope 93 is bonded to the bending envelope 85 via a bonding portion 86 such as an adhesive. As described above, the first flexible tube section 23 is coupled with the bending section 22. The first helical tube 91, the first flexible reticular tube 92 and the first flexible envelope 93, which are inserted into an inner peripheral side of the support member 51, are fitted into the support member 51. Consequently, the second flexible tube section 25 is coupled with the base section 27. Additionally, in the present embodiment, the first helical tube 91, the first flexible reticular tube 92 and the first flexible envelope 93 are continuously extended between the first flexible tube section 23 and the second flexible tube section 25.

As shown in FIG. 6, the first helical tube 91 includes a band member 95 made of a metal. In the first helical tube 91, the band member 95 is helically extended around the longitudinal axis C. The first flexible reticular tube 92 includes a wire 96 made of a metal. In the first flexible reticular tube 92, the wire 96 is knitted. The first flexible envelope 93 is made of a resin material.

As shown in FIG. 4, the third flexible tube section 26 is constituted of a second helical tube 101 that is a second flex, a second flexible reticular tube 102 that is a second flexible blade, and a second flexible envelope 103. The second helical tube 101, the second flexible reticular tube 102 and the second flexible envelope 103 are extended along the longitudinal axis C from a distal end of the third flexible tube section 26 to a proximal end of the third flexible tube section 26. An outer peripheral side of the second helical tube 101 is covered with the second flexible reticular tube 102, and an outer peripheral side of the second flexible reticular tube 102 is covered with the second flexible envelope 103. The proximal portion of the support member 51 is fitted into a connecting member 104. The second helical tube 101 and the second flexible reticular tube 102, which are inserted into an inner peripheral side of the connecting member 104, are fitted into the connecting member 104. In consequence, the third flexible tube section 26 is coupled with the base section 27.

In the second helical tube 101, a band member 105 made of a metal is helically extended around the longitudinal axis C. Additionally, in the second flexible reticular tube 102, a wire 106 made of a metal is knitted. The second flexible envelope 103 is made of a resin material. It is to be noted that in FIG. 6, constitutions concerned with the first flexible tube section 23 and the second flexible tube section 25 are denoted with reference signs without parentheses and constitutions concerned with the third flexible tube section 26 are denoted with reference signs within parentheses.

In the state where the rotary unit 30 is attached to the inserting section 3, the outer rollers 65A to 65F that are the driving force receiving portions are positioned on the outer peripheral side of the base section 27. Consequently, in the state where the rotary unit 30 is attached to the inserting section 3, a proximal end of the rotary unit 30 is positioned on the outer peripheral side of the base section 27. Further, the rotary unit 30 is extended toward the distal direction from a region located on the outer peripheral side of the base section 27. Consequently, in the state where the rotary unit 30 is attached to the inserting section 3, an outer peripheral side of the third flexible tube section 26 is not covered with the rotary unit 30.

Additionally, in the state where the rotary unit 30 is attached to the inserting section 3, an outer peripheral side of the second flexible tube section 25 is covered with the spiral tube 31 of the rotary unit 30. Further, a distal end of the rotary unit 30 is positioned in an area between the first flexible tube section 23 and the second flexible tube section 25 in the axis parallel direction parallel to the longitudinal axis C. Consequently, in the state where the rotary unit 30 is attached to the inserting section 3, an outer peripheral side of the first flexible tube section 23 is not covered with the rotary unit 30.

In the bending section 22, the bending tube 81 easy to bend perpendicularly to the longitudinal axis C is provided and the bending envelope 85 is made of a material having a high flexibility. Consequently, and thereby the bending section 22 has a flexibility higher than each of the first flexible tube section 23, the second flexible tube section 25 and the third flexible tube section 26. Additionally, the spiral tube 31 of the rotary unit 30 is made of a resin having a high flexibility, and thereby has a flexibility higher than each of the first flexible tube section 23, the second flexible tube section 25 and the third flexible tube section 26.

The first flexible tube section 23, the second flexible tube section 25 and the third flexible tube section 26 change in accordance with an inner diameter of the helical tube (91, 101), a thickness of the band member (95, 105) in the helical tube (91, 101), the number of layers of the helical tube (91, 101), a diameter of the wire (96, 106) in the flexible reticular tube (92, 102), a thickness of the flexible envelope (93, 103), an outer diameter of the flexible tube section (23, 25, or 26), a hardness of the resin that forms the flexible envelope (93, 103), or the like. The larger the inner diameter of the helical tube (91, 101) is, the lower the flexibility of the flexible tube section (23, 25, or 26) becomes, and the larger the thickness of the band member (95, 105) is, the lower the flexibility of the flexible tube section (23, 25, or 26) becomes. Additionally, the larger the number of the layers of the helical tube (91, 101) is, the lower the flexibility of the flexible tube section (23, 25, or 26) becomes, and the larger the diameter of the wire (96, 106) is, the lower the flexibility of the flexible tube section (23, 25, or 26) becomes. Further, the larger the outer diameter is, the lower the flexibility of the flexible tube section (23, 25, or 26) becomes, and the larger the thickness of the flexible envelope (93, 103) is, the lower the flexibility of the flexible tube section (23, 25, or 26) becomes. Additionally, the higher the hardness of the resin in the flexible envelope (93, 103) is, the higher the flexibility of the flexible tube section (23, 25, or 26) becomes.

In a certain example, in a state where the rotary unit 30 is not attached to the inserting section 3, the first flexible tube section 23 has a flexibility equal to the second flexible tube section 25. Additionally, in another example, in the state where the rotary unit 30 is not attached to the inserting section 3, the second flexible tube section 25 has a flexibility higher than the first flexible tube section 23. For example, by changing the hardness of the resin of the first flexible envelope 93 between the first flexible tube section 23 and the second flexible tube section 25, the first flexible tube section 23 has a flexibility different from that of the second flexible tube section 25. According to the present embodiment, in any cases including the abovementioned examples, in a state where the second flexible tube section 25 is not covered with the spiral tube 31, the second flexible tube section 25 has a flexibility equal to the first flexible tube section 23 or higher than the first flexible tube section 23. Additionally, also in the state where the second flexible tube section 25 is not covered with the spiral tube 31, the second flexible tube section 25 has a flexibility lower than the spiral tube 31 and the bending section 22.

It is to be noted that in the first flexible tube section 23 and the second flexible tube section 25, the inner diameter of the first helical tube 91 is adjusted in a range of 9.4 mm to 9.8 mm and the thickness of the band member 95 is adjusted in a range of 0.20 mm to 0.28 mm. Additionally, in the first flexible tube section 23 and the second flexible tube section 25, the number of the layers of the first helical tube 91 is one and the diameter of the wire 96 is adjusted in a range of 0.08 mm to 0.12 mm. Further, in the first flexible tube section 23 and the second flexible tube section 25, the thickness of the first flexible envelope 93 is adjusted in a range of 0.4 mm to 0.8 mm and the outer diameter is adjusted in a range of 11.5 mm to 11.9 mm.

As described above, the rotary unit 30 is attached to the inserting section 3, whereby the outer peripheral side of the second flexible tube section 25 is covered with the spiral tube 31. In this state, the first flexible tube section 23 and the third flexible tube section 26 are not covered with the rotary unit 30. In the state where the outer peripheral side of the second flexible tube section 25 is covered with the spiral tube 31, the second flexible tube section 25 has a flexibility lower than the first flexible tube section 23. However, the spiral tube 31 has a flexibility higher than the first flexible tube section 23 and the second flexible tube section 25, and the second flexible tube section 25 has a flexibility equal to the first flexible tube section 23 or higher than the first flexible tube section 23. Consequently, also in the state where the second flexible tube section 25 is covered with the spiral tube 31, the flexibility of the second flexible tube section 25 does not become excessively low as compared to the first flexible tube section 23.

In the third flexible tube section 26, the flexibility becomes lower than in the first flexible tube section 23 and the second flexible tube section 25, along its total length in the axis parallel direction parallel to the longitudinal axis C. Inside the inserting section 3, the guide channel 78 and the driving shaft 79 are extended toward the distal direction up to the hollow portion 52 defined by the support member 51. That is, inside the third flexible tube section 26, there are extended the guide channel 78 and the driving shaft 79 which are not extended inside the first flexible tube section 23 and the second flexible tube section 25. Consequently, in the third flexible tube section 26, the number of inside-extended members (e.g., the imaging cable 41, the light guide 42, etc.) to be extended inside increases as compared with the first flexible tube section 23 and the second flexible tube section 25. The number of the inside-extended members to be extended inside increases, whereby in the third flexible tube section 26, it is necessary to increase a sectional area of a formed inner space which is perpendicular to the longitudinal axis C as compared with the first flexible tube section 23 and the second flexible tube section 25. Consequently, in the third flexible tube section 26, it is necessary to increase the inner diameter of the first helical tube 91 as compared with the second helical tube 101 of the first flexible tube section 23 and the second flexible tube section 25, and it is necessary to increase the outer diameter of the third flexible tube section as compared with the first flexible tube section 23 and the second flexible tube section 25. The abovementioned term is defined as one factor in addition to the thickness of the band member 105, the thickness of the second flexible envelope 103 and the like, and thereby the third flexible tube section 26 has a flexibility lower than each of the first flexible tube section 23 and the second flexible tube section 25.

In the third flexible tube section 26, the flexibility decreases from the distal direction toward the proximal direction. For example, by increasing the thickness of the second flexible envelope 103 from the distal direction toward the proximal direction, a proximal portion of the third flexible tube section 26 has a flexibility different from that of the distal portion of the third flexible tube section. In the third flexible tube section 26, the inner diameter of the second helical tube 101 is adjusted in a range of 10.7 mm to 11.0 mm and the thickness of the band member 105 is adjusted in a range of 0.28 mm to 0.32 mm. Additionally, in the third flexible tube section 26, the number of the layers of the second helical tube 101 is one or two and the diameter of the wire 106 is adjusted in a range of 0.10 mm to 0.12 mm. Further, in the third flexible tube section 26, the thickness of the second flexible envelope 103 is adjusted in a range of 0.35 mm to 0.6 mm and the outer diameter thereof is adjusted in a range of 12.7 mm to 13.2 mm.

Here, a state where the inner diameter of the second helical tube 101 is 11 mm, the thickness of the band member 105 is 0.32 mm, the number of the layers of the second helical tube 101 is two, the diameter of the wire 106 is 0.12 mm, the thickness of the second flexible envelope 103 is 0.6 mm and the outer diameter of the third flexible tube section 26 is 13.2 mm is defined as a minimum flexible state of the third flexible tube section 26. In the third flexible tube section 26, even the proximal end having the lowest flexibility has a flexibility equal to the minimum flexible state or higher than the minimum flexible state. Therefore, in the third flexible tube section 26, the flexibility does not become excessively low.

Additionally, also in the state where the second flexible tube section 25 is covered with the spiral tube 31, the second flexible tube section has a flexibility approximately equal to the distal portion of the third flexible tube section 26. Therefore, also in the second flexible tube section 25 covered with the spiral tube 31, the flexibility is higher than the minimum flexible state of the third flexible tube section 26, and the flexibility does not become excessively low. Here, a state where the flexibility is approximately equal is not limited to a state where the flexibility of the second flexible tube section 25 covered with the spiral tube 31 is equal to the flexibility of the distal portion of the third flexible tube section 26. That is, the state where the flexibility is approximately equal includes a state where the flexibility of the distal portion of the third flexible tube section 26 is slightly higher than the flexibility of the second flexible tube section 25 covered with the spiral tube 31, and a state where the flexibility of the distal portion of the third flexible tube section 26 is slightly lower than the flexibility of the second flexible tube section 25 covered with the spiral tube 31. The flexibility of the third flexible tube section 26 is set as described above, and hence in the third flexible tube section 26, the flexibility does not become excessively high or the flexibility does not become excessively low as compared to the second flexible tube section 25 covered with the spiral tube 31. Additionally, the first flexible tube section 23 has a flexibility higher than the distal portion of the third flexible tube section 26, and hence in the first flexible tube section 23, the flexibility does not become excessively low as compared to the bending section 22.

Figure 7:
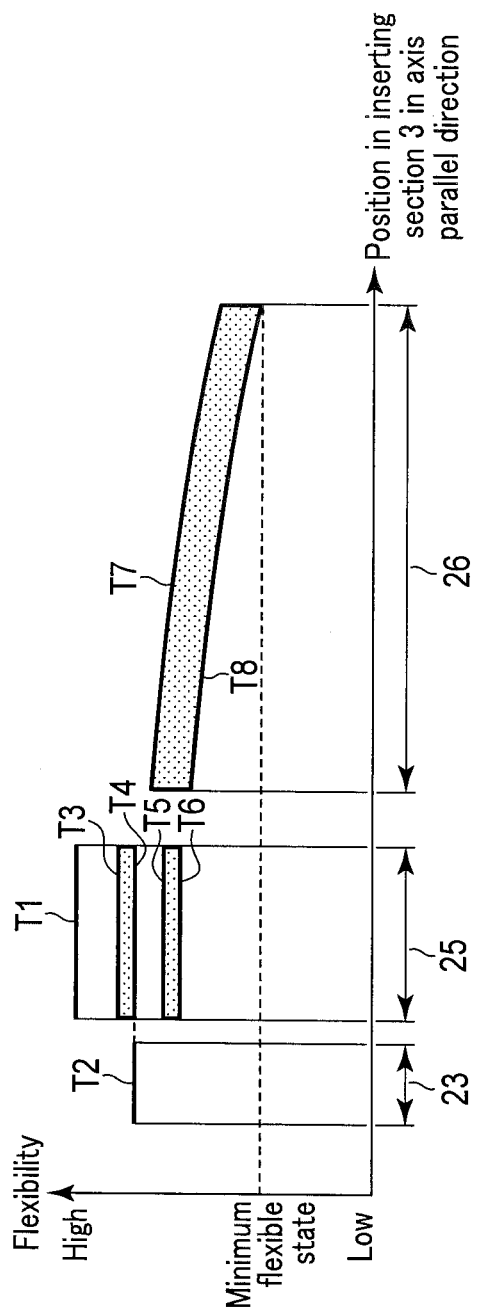
FIG. 7 is a schematic diagram showing flexibilities of the first flexible tube section, the second flexible tube section, the third flexible tube section and a spiral tube according to the first embodiment.

FIG. 7 is a diagram showing flexibilities of the first flexible tube section 23, the second flexible tube section 25, the third flexible tube section 26 and the spiral tube 31. In FIG. 7, the flexibility of the spiral tube 31 is shown by a straight line T1. Further, the flexibility of the first flexible tube section 23 is shown by a straight line T2. Additionally, the flexibility of the second flexible tube section 25 that is not covered with the spiral tube 31 is adjusted in a range between a straight line T3 and a straight line T4. Therefore, as described above, the spiral tube 31 has a flexibility higher than each of the first flexible tube section 23 and the second flexible tube section 25. Additionally, the flexibility of the second flexible tube section 25 that is not covered with the spiral tube 31 is equal to the flexibility of the first flexible tube section 23 or higher than the flexibility of the first flexible tube section 23.

Additionally, the flexibility of the second flexible tube section 25 is adjusted as described above, and hence the flexibility of the second flexible tube section 25 covered with the spiral tube 31 is in a range between a straight line T5 and a straight line T6. Further, the flexibility of the third flexible tube section 26 is adjusted in a range between a straight line T7 and a straight line T8. Therefore, as described above, the second flexible tube section 25 covered with the spiral tube 31 has a flexibility approximately equal to the distal portion of the third flexible tube section 26. Further, the proximal end of the third flexible tube section 26 has a flexibility equal to the minimum flexible state or higher than the minimum flexible state.

In addition, the base section 27 is hard, because the support member 51 is made of a metal. Consequently, the base section 27 has a flexibility lower than the third flexible tube section 26 and a flexibility lower than in the minimum flexible state. Additionally, a fourth axis parallel dimension L4 of the base section 27 in the axis parallel direction parallel to the longitudinal axis C is small. Consequently, there is hardly any influence of the flexibility of the base section 27 onto the movability of the inserting section 3 along the longitudinal axis C in the lumen.

Next, there will be described a function and an effect of the endoscope apparatus 1 that is the inserting apparatus including the rotary unit 30 and the endoscope 2 that is the inserting instrument of the present embodiment. When the endoscope apparatus 1 is used, the inserting section 3 and the rotary unit 30 are inserted into the lumen in the state where the rotary unit 30 is attached to the inserting section 3. Further, the motor 72 is driven in a state where the fin portion 33 of the spiral tube 31 abuts on the lumen wall, whereby the rotation driving force is transmitted to the driving force transmission unit 53 attached to the base section 27 of the inserting section 3 as described above. Further, the driving force transmission unit 53 is driven, and the outer rollers 65A to 65F that are the driving force receiving portions receive the rotation driving force from the driving force transmission unit 53. Consequently, the rotary unit 30 rotates about the longitudinal axis C. The rotary unit 30 rotates around the longitudinal axis C in the state where the fin portion 33 of the spiral tube 31 is pressed toward the inner peripheral direction by the lumen wall or the like, whereby the impulsive force toward the distal direction or the proximal direction is applied to the inserting section 3 and the rotary unit 30.

Here, FIG. 8 shows a first comparative example as a comparison with the present embodiment. In the first comparative example shown in FIG. 8, differently from the present embodiment, a flexibility of a first flexible tube section 23A becomes excessively low as compared to a bending section 22A. As shown in FIG. 8, in a lumen such as an inner part of a small intestine or an inner part of a large intestine, a lumen bending site B0 in which the lumen bends is present. In the lumen bending site B0, the lumen bends from a first lumen extending direction (a direction of an arrow B1 of FIG. 8) toward a second lumen extending direction (a direction of an arrow B2 of FIG. 8). Consequently, in the lumen bending site B0, an inserting direction of an inserting section 3A changes from the first lumen extending direction to the second lumen extending direction.

In a case where, in the lumen, an impulsive force toward a distal direction (the inserting direction) is applied to the inserting section 3A from a state where the distal end of the first flexible tube section 23A is positioned in the lumen bending site B0, the impulsive force is applied to the first flexible tube section 23A toward a first lumen extending direction B1. Consequently, the first flexible tube section 23A moves toward the first lumen extending direction B1, and in the lumen bending site B0, an acting force from the first flexible tube section 23A toward the first lumen extending direction B1 acts on a lumen wall. Here, the flexibility of the first flexible tube section 23A becomes excessively low as compared to the bending section 22A, and hence in the lumen bending site B0, the first flexible tube section 23A is hard to bend into a shape along the lumen, and there excessively increases the acting force toward the first lumen extending direction B1 which acts on the lumen wall from the first flexible tube section 23A in the lumen bending site B0. A large acting force acts from the first flexible tube section 23A in the first lumen extending direction B1, whereby the lumen wall moves toward the first lumen extending direction B1 in the lumen bending site B0, and a stick phenomenon disadvantageously occurs. By the occurrence of the stick phenomenon, there deteriorates a movability of the first flexible tube section 23A from the lumen bending site B0 toward the second lumen extending direction B2. In consequence, there deteriorates the movability of the inserting section 3A toward the distal direction from the state where the distal end of the first flexible tube section 23A is positioned in the lumen bending site B0.

On the other hand, FIG. 9 shows a state where the impulsive force toward the distal direction is applied to the inserting section 3 in a state where the distal end of the first flexible tube section 23 of the present embodiment is positioned in a lumen bending site B0. In the present embodiment, the first flexible tube section 23 has a flexibility higher than the third flexible tube section 26 and has a flexibility higher than the second flexible tube section 25 covered with the spiral tube 31. Consequently, in the first flexible tube section 23, the flexibility does not become excessively low as compared to the bending section 22.

As described above, the flexibility of the first flexible tube section 23 is adjusted, and hence, as shown in FIG. 9, also in a case where the impulsive force in a first lumen extending direction B1 (the distal direction) is applied to the first flexible tube section 23 from a state where the distal end of the first flexible tube section 23 is positioned in the lumen bending site B0, the first flexible tube section 23 is easy to bend into a shape along the lumen in the lumen bending site B0. Additionally, an acting force that acts on the lumen wall from the first flexible tube section 23 toward the first lumen extending direction B1 in the lumen bending site B0 does not increase, and a stick phenomenon is hard to occur in the lumen bending site B0. Consequently, it is possible to acquire a movability of the first flexible tube section 23 along the lumen (the longitudinal axis C) in the lumen bending site B0. That is, it is possible to acquire the movability of the first flexible tube section 23 toward a second lumen extending direction B2 from the state where the distal end of the first flexible tube section 23 is positioned in the lumen bending site B0.

Additionally, FIG. 10 shows a second comparative example as a comparison with the present embodiment. In the second comparative example shown in FIG. 10, differently from the present embodiment, a flexibility of a second flexible tube section 25B covered with a spiral tube 31B becomes excessively low as compared to a first flexible tube section 23B. In a case where an impulsive force toward a distal direction (an inserting direction) is applied to an inserting section 3B in a state where a distal end of the second flexible tube section 25B is positioned in a lumen bending site B0 in a lumen, the impulsive force is applied to the second flexible tube section 25B toward a first lumen extending direction B1. Consequently, the second flexible tube section 25B moves in the first lumen extending direction B1, and an acting force toward the first lumen extending direction B1 acts on a lumen wall from the second flexible tube section 25B in the lumen bending site B0. The flexibility of the second flexible tube section 25B covered with the spiral tube 31B becomes excessively low as compared to the first flexible tube section 23B, and hence the second flexible tube section 25B and the spiral tube 31B are hard to bend into a shape along the lumen in the lumen bending site B0, and there excessively increases the acting force toward the first lumen extending direction B1 which acts on the lumen wall from the second flexible tube section 25B in the lumen bending site B0. In consequence, the abovementioned stick phenomenon disadvantageously occurs. By the occurrence of the stick phenomenon, there deteriorates a movability of the second flexible tube section 25B and the spiral tube 31B from the lumen bending site B0 toward a second lumen extending direction B2. In consequence, there deteriorates a movability of the inserting section 3B toward the distal direction from the state where the distal end of the second flexible tube section 25B is positioned in the lumen bending site B0.

On the other hand, FIG. 11 shows a state where the impulsive force toward the distal direction is applied to the inserting section 3 in a state where the distal end of the second flexible tube section 25 of the present embodiment is positioned in a lumen bending site B0. In the present embodiment, the spiral tube 31 has a flexibility higher than the first flexible tube section 23 and the second flexible tube section 25, and the second flexible tube section 25 has a flexibility equal to the first flexible tube section 23 or higher than the first flexible tube section 23. Further, the flexibility of the second flexible tube section 25 covered with the spiral tube 31 is approximately equal to the flexibility of the distal portion of the third flexible tube section 26. Consequently, also in the state where the second flexible tube section 25 is covered with the spiral tube 31, the flexibility of the second flexible tube section does not become excessively low as compared to the first flexible tube section 23.

The flexibility of the second flexible tube section 25 is adjusted as described above, and hence, as shown in FIG. 11, also in a case where the impulsive force toward a first lumen extending direction B1 (the distal direction) is applied to the second flexible tube section 25 in a state where the distal end of the second flexible tube section 25 is positioned in the lumen bending site B0, the second flexible tube section 25 covered with the spiral tube 31 is easy to bend into a shape along the lumen in the lumen bending site B0. Additionally, an acting force that acts on the lumen wall from the second flexible tube section 25 toward the first lumen extending direction B1 in the lumen bending site B0 does not increase, and a stick phenomenon is hard to occur in the lumen bending site B0. Consequently, it is possible to acquire a movability of the second flexible tube section 25 covered with the spiral tube 31 along the lumen (the longitudinal axis C) in the lumen bending site B0. That is, it is possible to acquire the movability of the second flexible tube section 25 toward a second lumen extending direction B2 from the state where the distal end of the second flexible tube section 25 is positioned in the lumen bending site B0.

Additionally, FIG. 12 shows a third comparative example as a comparison with the present embodiment. In the third comparative example shown in FIG. 12, differently from the present embodiment, a flexibility of a third flexible tube section 26C becomes excessively high as compared to a second flexible tube section 25C covered with a spiral tube 31C. The flexibility becomes excessively high in the third flexible tube section 26C, and hence also in a case where an impulsive force toward a distal direction is applied to an inserting section 3C in a state where a distal portion of the third flexible tube section 26C is positioned in a lumen bending site B0 in a lumen, an impulsive force becoming excessively small in a first lumen extending direction B1 is applied to the third flexible tube section 26C. The impulsive force toward the first lumen extending direction B1 applied to the third flexible tube section 26C decreased, thereby decreasing an acting force toward an opposite direction to the first lumen extending direction B1 (a proximal direction) which acts on a lumen wall from the distal portion of the third flexible tube section 26C. Consequently, the lumen wall does not move from an area located on an outer peripheral side of the distal portion of the third flexible tube section 26C toward a pullout direction (the opposite direction to the first lumen extending direction B1). In consequence, pleats of the lumen wall are densely formed in the area of the outer peripheral side of the distal portion of the third flexible tube section 26C, and a movability of the lumen wall in the pullout direction deteriorates. The movability of the lumen wall toward the pullout direction deteriorates, whereby a movability of the third flexible tube section 26C toward a second lumen extending direction B2 deteriorates. In consequence, there deteriorates a movability of the inserting section 3C toward the distal direction from the state where the distal portion of the third flexible tube section 26C is positioned in the lumen bending site B0.

On the other hand, FIG. 13 shows a state where an impulsive force toward a distal direction is applied to the inserting section 3 in a state where the distal portion of the third flexible tube section 26 of the present embodiment is positioned in a lumen bending site B0. In the present embodiment, the third flexible tube section 26 has a flexibility lower than the first flexible tube section 23. Consequently, in the third flexible tube section 26, the flexibility does not become excessively high as compared to the second flexible tube section 25 covered with the spiral tube 31.

The flexibility of the third flexible tube section 26 is adjusted as described above, and hence, as shown in FIG. 13, also in a case where the impulsive force toward the distal direction (the inserting direction) is applied to the inserting section 3 from a state where the distal end of the third flexible tube section 26 is positioned in the lumen bending site B0, the impulsive force toward a first lumen extending direction B1 which is applied to the third flexible tube section 26 does not become excessively small. Consequently, in the lumen bending site B0, an acting force toward a proximal direction (an opposite direction to the first lumen extending direction B1) appropriately acts on the lumen wall from the distal portion of the third flexible tube section 26. In consequence, the lumen wall moves from an area located on the outer peripheral side of the distal portion of the third flexible tube section 26 toward a pullout direction (the opposite direction to the first lumen extending direction B1), and the pleats of the lumen wall are prevented from being densely formed in the area of the outer peripheral side of the distal portion of the third flexible tube section 26. Therefore, it is possible to acquire a movability of the third flexible tube section 26 along the lumen (the longitudinal axis C) in the lumen bending site B0. That is, it is possible to acquire the movability of the third flexible tube section 26 toward a second lumen extending direction B2 from the state where the distal portion of the third flexible tube section 26 is positioned in the lumen bending site B0.

Additionally, the third flexible tube section 26 has a flexibility equal to the abovementioned minimum flexible state or higher than the minimum flexible state, even at its proximal end having the lowest flexibility in the third flexible tube section 26. In addition, the distal portion of the third flexible tube section 26 has a flexibility approximately equal to the second flexible tube section 25 covered with the spiral tube 31. Consequently, in the third flexible tube section 26, the flexibility does not become excessively low as compared to the second flexible tube section 25 covered with the spiral tube 31.

The flexibility of the third flexible tube section 26 does not become excessively low as described above, and hence also in a case where the impulsive force toward the first lumen extending direction B1 (the distal direction) is applied to the third flexible tube section 26 in the state where the distal end of the third flexible tube section 26 is positioned in the lumen bending site B0, the third flexible tube section 26 is easy to bend into the shape along the lumen in the lumen bending site B0. Additionally, the abovementioned stick phenomenon is hard to occur in the lumen bending site B0. Consequently, it is possible to more securely acquire the movability of the third flexible tube section 26 along the lumen (the longitudinal axis C) in the lumen bending site B0.

The flexibilities of the first flexible tube section 23, the second flexible tube section 25, the third flexible tube section 26 and the spiral tube 31 are adjusted as described above, and hence also in the state where the rotary unit 30 is rotatably attached to the inserting section 3, it is possible to acquire the movability of the inserting section 3 along the longitudinal axis C in the lumen bending site B0 of the lumen.

(Modifications)

It is to be noted that, in the first embodiment, the first flexible tube section 23 and the second flexible tube section 25 are constituted of the same members (the first helical tube 91, the first flexible reticular tube 92 and the first flexible envelope 93), but it is not limited to this embodiment. For example, FIG. 14 shows a first modification as a modification. In the first modification, a first flexible tube section 23 includes a first helical tube 111, a first flexible reticular tube 112 and a first flexible envelope 113. Additionally, a second flexible tube section 25 includes a second helical tube 115, a second flexible reticular tube 116 and a second flexible envelope 117. Further, a third flexible tube section 26 includes a third helical tube 121, a third flexible reticular tube 122 and a third flexible envelope 123. According to the abovementioned constitution, the first flexible tube section 23 is constituted of members separate from those of the second flexible tube section 25.

The first helical tube 111, the second helical tube 115 and the third helical tube 121 are constituted of band members (95, 105) made of a metal in the same manner as in the helical tubes (91, 101) of the first embodiment. The first flexible reticular tube 112, the second flexible reticular tube 116 and the third flexible reticular tube 122 are constituted of wires (96, 106) made of a metal in the same manner as in the flexible reticular tubes (92, 102) of the first embodiment. Further, the first flexible envelope 113, the second flexible envelope 117 and the third flexible envelope 123 are made of a resin in the same manner as in the flexible envelopes (93, 103) of the first embodiment.

The second helical tube 115 and the second flexible reticular tube 116, which are inserted into an inner peripheral side of the first helical tube 111, are fitted into the first helical tube 111 and the first flexible reticular tube 112. Additionally, the first flexible envelope 113 is bonded to the second flexible envelope 117 via a bonding portion 118 such as an adhesive. As described above, the first flexible tube section 23 is coupled with the second flexible tube section 25. The second helical tube 115, the second flexible reticular tube 116 and the second flexible envelope 117, which are inserted into an inner peripheral side of a support member 51, are fitted into the support member 51. Consequently, the second flexible tube section 25 is coupled with a base section 27. Additionally, the third helical tube 121, the third flexible reticular tube 122 and the third flexible envelope 123, which are inserted into the inner peripheral side of the support member 51, are fitted into the support member 51. In consequence, the third flexible tube section 26 is coupled with the base section 27.

Also in the present modification, similarly to the first embodiment, a spiral tube 31 has a flexibility higher than each of the first flexible tube section 23 and the second flexible tube section 25. Additionally, the second flexible tube section 25 has a flexibility equal to the first flexible tube section 23 or higher than the first flexible tube section 23. Further, the second flexible tube section 25 is covered with the spiral tube 31, whereby a flexibility of the second flexible tube section is lower than that of the first flexible tube section 23. Additionally, the third flexible tube section 26 has a flexibility lower than the first flexible tube section 23, and a distal portion of the third flexible tube section 26 has a flexibility approximately equal to the second flexible tube section 25 covered with the spiral tube 31.

Additionally, in the first embodiment, the bending section 22 is constituted only of the active bending section that bends by the bending operation, but it is not limited to this embodiment. For example, as shown as a second modification in FIG. 15, a bending section 22 may include an active bending section 125 and a passive bending section 126. The active bending section 125 actively bends by a bending operation. On the other hand, the passive bending section 126 is passively bent by applying an external force thereto. The passive bending section 126 is continuous with a proximal direction side of the active bending section 125.

The active bending section 125 includes an active bending tube 128 constituted of bending pieces 127. Additionally, the passive bending section 126 includes a passive bending tube 132 constituted of bending pieces 131. The active bending tube 128 and the passive bending tube 132 are formed in the same manner as in the bending tube 81 of the first embodiment. The passive bending tube 132, which is inserted into an inner peripheral side of the active bending tube 128, is fitted into the active bending tube 128. Outer peripheral sides of the active bending tube 128 and the passive bending tube 132 are covered with a bending reticular tube 133. An outer peripheral side of the bending reticular tube 133 is covered with a bending envelope 135. The bending reticular tube 133 is formed in the same manner as in the bending reticular tube 83 of the first embodiment, and the bending envelope 135 is formed in the same manner as in the bending envelope 85 of the first embodiment.

Additionally, in the first embodiment, the base section 27 is disposed between the second flexible tube section 25 and the third flexible tube section 26, but it is not limited to this embodiment. For example, as shown as a third modification in FIG. 16, a base section 27 may be provided between a first flexible tube section 23 and a second flexible tube section 25. Also in the present modification, an outer peripheral side of the second flexible tube section 25 is covered with a spiral tube 31 in a state where a rotary unit 30 is attached to an inserting section 3. Further, the first flexible tube section 23 and a third flexible tube section 26 are not covered with the rotary unit 30.

Also in the present modification, a driving force transmission unit 53 is attached to the base section 27. Further, in the rotary unit 30, there are provided driving force receiving portions that receive a rotation driving force from the driving force transmission unit 53 (e.g., a constitution similar to the outer rollers 65A to 65F of the first embodiment). However, in the present modification, differently from the first embodiment, the driving force receiving portions (65A to 65F) are provided in a distal side cylindrical portion 35, and positioned on a distal direction side with respect to the spiral tube 31. Therefore, in the present modification, the rotary unit 30 is extended from the driving force receiving portions (65A to 65F) toward a proximal direction.

It is to be noted that also in the present modification, flexibilities of the spiral tube 31, the first flexible tube section 23, the second flexible tube section 25 and the third flexible tube section 26 are adjusted in the same manner as in the first embodiment.

Additionally, in the abovementioned embodiments and modifications, the endoscope apparatus 1 that is the inserting apparatus including the endoscope 2 as the inserting instrument has been described, but it is also applicable to an inserting apparatus including, for example, a manipulator as the inserting instrument.

In the abovementioned embodiment and modifications, the first flexible tube section (23) and the second flexible tube section (25) provided on the proximal direction side with respect to the first flexible tube section (23) have a flexibility lower than the spiral tube (31). Further, in the state where the rotary unit (30) is attached to the inserting section (3), the outer peripheral side of the second flexible tube section (25) is covered with the spiral tube (31). In the state where the second flexible tube section is not covered with the spiral tube (31), the second flexible tube section (25) has a flexibility equal to the first flexible tube section (23) or higher than the first flexible tube section (23). Further, the outer peripheral side of the second flexible tube section is covered with the spiral tube (31), whereby the flexibility of the second flexible tube section (25) becomes lower than that of the first flexible tube section (23). Additionally, in the third flexible tube section (26) provided on the proximal direction side with respect to the second flexible tube section (25), the flexibility of the third flexible tube section becomes lower than that of the first flexible tube section (23).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inserting instrument to which a rotary unit including a spiral tube is rotatably attached around a longitudinal axis, the inserting instrument comprising: an inserting section extended along the longitudinal axis, and inserted through the rotary unit; a bending section provided in a distal portion of the inserting section, the bending section comprising a bending tube, the bending tube comprising a plurality of bending pieces, each of the plurality of bending pieces being rotatably coupled to an adjacent bending piece; a first flexible tube section provided on a proximal side with respect to the bending section in the inserting section, and having a flexibility lower than both of a flexibility of the spiral tube and a flexibility of the bending section; a second flexible tube section provided on the proximal side with respect to the first flexible tube section in the inserting section, and covered by the spiral tube from an outer peripheral side in a state where the rotary unit is attached to the inserting section, the second flexible tube section having a flexibility lower than the flexibility of the spiral tube, the flexibility of the second flexible tube section being equal to the flexibility of the first flexible tube section or higher than the flexibility of the first flexible tube section in a state where the second flexible tube section is not covered by the spiral tube, a flexibility of a region in which the spiral tube covers the second flexible tube section being lower than that of the first flexible tube section in the state where the rotary unit is attached to the inserting section; a first helical tube comprising a first band portion comprising a metal, the first band portion being helically extended around the longitudinal axis in the first helical tube, the first helical tube continuously extending from the first flexible tube section to the second flexible tube section along the longitudinal axis; and a third flexible tube section provided on the proximal side with respect to the second flexible tube section in the inserting section, and having a flexibility lower than the flexibility of the first flexible tube section, the flexibility of the third flexible tube decreasing from a distal side toward the proximal side, a sectional area of an inner space of the third flexible tube section perpendicular to the longitudinal axis being larger than both of a sectional area of an inner space of the first flexible tube section perpendicular to the longitudinal axis and a sectional area of an inner space of the second flexible tube section perpendicular to the longitudinal axis, an inner diameter of the third flexible tube section being larger than both of an inner diameter of the first flexible tube section and an inner diameter of the second flexible tube section, an outer diameter of the third flexible tube section being larger than both of an outer diameter of the first flexible tube section and an outer diameter of the second flexible tube section, wherein the flexibility of the region in which the spiral tube covers the second flexible tube section in the state where the rotary unit is attached to the inserting section is higher than a flexibility at a proximal end of the third flexible tube section.

2. The inserting instrument of claim 1, wherein the flexibility of the region in which the spiral tube covers the second flexible tube section in the state where the rotary unit is attached to the inserting section is in a range between a minimum value and a maximum value of a flexibility at a distal end of the third flexible tube section.

3. The inserting instrument of claim 1, further comprising:
a base section which is provided in the inserting section in a state where the base section is positioned between the second flexible tube section and the third flexible tube section in an axis parallel direction parallel to the longitudinal axis, which has a flexibility lower than the flexibility of the third flexible tube section, and in which a driving force receiving portion provided on the proximal side with respect to the spiral tube in the rotary unit is positioned on the outer peripheral side in the state where the rotary unit is attached to the inserting section; and
a driving force transmission unit attached to the base section, configured to be driven by transmission of a rotation driving force to rotate the rotary unit, and configured to be driven in the state where the rotary unit is attached to the inserting section, thereby transmitting the rotation driving force to the driving force receiving portion.

4. The inserting instrument of claim 1,
wherein a first axis parallel dimension of the first flexible tube section in an axis parallel direction parallel to the longitudinal axis is smaller than a second axis parallel dimension of the second flexible tube section in the axis parallel direction, and
the second axis parallel dimension is smaller than a third axis parallel dimension of the third flexible tube section in the axis parallel direction.

5. A rotary unit which is rotatably attached to the inserting section of the inserting instrument of claim 1 around the longitudinal axis, the rotary unit including: the spiral tube covering the outer peripheral side of the second flexible tube section in the state where the rotary unit is attached to the inserting section, and having a flexibility higher than a flexibility of the second flexible tube section.

6. An inserting apparatus comprising: the inserting instrument of claim 1; and the rotary unit rotatably attached to the inserting section of the inserting instrument around the longitudinal axis, and including the spiral tube covering the outer peripheral side of the second flexible tube section in the state where the rotary unit is attached to the inserting section and having a flexibility higher than a flexibility of the second flexible tube section.

7. The inserting instrument of claim 1, wherein the third flexible tube section comprises a second helical tube, the second helical tube comprising a second band portion comprising a metal, the second band portion being helically extended around the longitudinal axis in the second helical.

8. The inserting instrument of claim 7,
wherein the third flexible tube section includes a flexible reticular tube including a reticularly knitted wire made of a metal and covering the outer peripheral side of the second helical tube, and a flexible envelope made of a resin and covering the outer peripheral side of the flexible reticular tube, and
in the case that a state where an inner diameter of the second helical tube is 11 mm, a thickness of the second band portion of the second helical tube is 0.32 mm, the number of layers of the second helical tube is two, a diameter of the wire of the flexible reticular tube is 0.12 mm, a thickness of the flexible envelope is 0.6 mm and the outer diameter of the third flexible tube section is 13.2 mm is defined as a minimum flexible state in which the flexibility is lowest, the flexibility at the proximal end of the third flexible tube section is equal to or higher than the minimum flexible state.

9. The inserting instrument of claim 1, wherein the rotary unit including the spiral tube does not cover both of the first flexible tube section and the third flexible tube section in the state where the rotary unit is attached to the inserting section.

* * * * *